US012005058B2

(12) United States Patent
Nielsen et al.

(10) Patent No.: US 12,005,058 B2
(45) Date of Patent: *Jun. 11, 2024

(54) NICOTINE TABLET

(71) Applicant: Fertin Pharma A/S, Vejle (DK)

(72) Inventors: Bruno Provstgaard Nielsen, Vejle Øst (DK); Kent Albin Nielsen, Brande (DK)

(73) Assignee: FERTIN PHARMA A/S, Vejle (DK)

( * ) Notice: Subject to any disclaimer, the term of this patent is extended or adjusted under 35 U.S.C. 154(b) by 0 days.

This patent is subject to a terminal disclaimer.

(21) Appl. No.: 18/348,891

(22) Filed: Jul. 7, 2023

(65) Prior Publication Data

US 2023/0346768 A1 Nov. 2, 2023

Related U.S. Application Data

(63) Continuation of application No. 16/213,641, filed on Dec. 7, 2018, now Pat. No. 11,738,016.

(30) Foreign Application Priority Data

Dec. 8, 2017 (DK) .............. PA 2017 70925

(51) Int. Cl.
| A61K 31/465 | (2006.01) |
| A61K 9/00 | (2006.01) |
| A61K 9/20 | (2006.01) |
| A61P 25/34 | (2006.01) |

(52) U.S. Cl.
CPC .......... *A61K 31/465* (2013.01); *A61K 9/0056* (2013.01); *A61K 9/006* (2013.01); *A61K 9/2009* (2013.01); *A61K 9/2027* (2013.01); *A61K 9/2095* (2013.01); *A61P 25/34* (2018.01)

(58) Field of Classification Search
CPC .... A61K 31/465; A61K 9/0056; A61K 9/006; A61K 9/2009; A61K 9/2027; A61K 9/2095; A61P 25/34
See application file for complete search history.

(56) References Cited

U.S. PATENT DOCUMENTS

| 4,866,046 | A | 9/1989 | Amer |
| 5,810,018 | A | 9/1998 | Monte |
| 5,935,604 | A | 8/1999 | Illum |
| 7,387,788 | B1 | 6/2008 | Carrara et al. |
| 8,529,939 | B2 | 9/2013 | Masters et al. |
| 8,597,679 | B2 | 12/2013 | Kolter et al. |
| 2001/0016593 | A1 | 8/2001 | Wilhelmsen |
| 2002/0002189 | A1 | 1/2002 | Smith et al. |
| 2006/0057207 | A1 | 3/2006 | Ziegler |
| 2007/0269386 | A1 | 11/2007 | Steen et al. |
| 2008/0286341 | A1 | 11/2008 | Andersson et al. |
| 2010/0108059 | A1 | 5/2010 | Axelsson et al. |
| 2010/0178353 | A1 | 7/2010 | Mezaache et al. |
| 2011/0206621 | A1 | 8/2011 | Agarwal et al. |
| 2011/0274628 | A1 | 11/2011 | Borschke |
| 2013/0177646 | A1 | 7/2013 | Hugerth et al. |
| 2013/0289079 | A1 | 10/2013 | Chen |
| 2014/0328973 | A1 | 11/2014 | Nielsen |
| 2015/0080442 | A1 | 3/2015 | McCarty |
| 2015/0096576 | A1 | 4/2015 | Gao et al. |
| 2017/0165252 | A1 | 6/2017 | Mua et al. |
| 2017/0172995 | A1 | 6/2017 | Repaka et al. |
| 2017/0189388 | A1 | 7/2017 | Arnold |
| 2019/0160019 | A1 | 5/2019 | Nielsen |
| 2019/0174812 | A1 | 6/2019 | Nielsen et al. |
| 2019/0175581 | A1 | 6/2019 | Nielsen et al. |
| 2020/0397691 | A1 | 12/2020 | Nielsen et al. |
| 2021/0345656 | A1 | 11/2021 | Nielsen et al. |
| 2023/0158011 | A1 | 5/2023 | Nielsen |

FOREIGN PATENT DOCUMENTS

| CA | 2831715 C | 10/2012 |
| EP | 1366759 A1 | 12/2003 |
| EP | 2177213 A1 | 4/2010 |
| EP | 2446881 A1 | 5/2012 |
| JP | 2006518761 A | 8/2006 |
| JP | 2010526876 A | 8/2010 |
| JP | 2011519862 A | 7/2011 |
| JP | 2012505878 A | 3/2012 |
| JP | 2014503539 A | 2/2014 |
| JP | 2015-503581 A | 2/2015 |
| RU | 2608902 C2 | 1/2017 |
| WO | WO2002085119 A1 | 10/2002 |
| WO | WO03055486 A1 | 7/2003 |
| WO | WO2003055486 A1 | 7/2003 |
| WO | WO2004075877 A1 | 9/2004 |
| WO | WO2007133140 A1 | 11/2007 |
| WO | WO2008037470 A1 | 4/2008 |
| WO | WO2008082808 A1 | 7/2008 |
| WO | WO2008140371 A1 | 11/2008 |
| WO | WO2008140372 A1 | 11/2008 |
| WO | WO2009007771 A1 | 1/2009 |
| WO | WO2009134947 A1 | 11/2009 |
| WO | WO2010044736 A1 | 4/2010 |
| WO | WO2012085043 A2 | 6/2012 |
| WO | WO2012134380 A1 | 10/2012 |
| WO | WO2013091631 A1 | 6/2013 |
| WO | WO2013103318 A1 | 7/2013 |
| WO | WO2019110072 A1 | 6/2019 |

OTHER PUBLICATIONS

"Cellulose, Microcrystalline," 2006. Eds. Rowe et al. In Handbook of Pharmaceutical Excipients, Fifth Edition, Pharmaceutical Press. London, England. pp. 132-135, 26 pages.

Conway, "Solid Dosage Forms", Mar. 2008. Ed. S. Cox In Pharmaceutical Manufacturing Handbook, Production and Processes, Chapter 4.1.11: Excerpt pp. 259-263.

(Continued)

*Primary Examiner* — Bethany P Barham
*Assistant Examiner* — Ayaan A Alam
(74) *Attorney, Agent, or Firm* — Lee & Hayes P.C.

(57) ABSTRACT

The invention relates to an orally disintegrating nicotine tablet for nicotine craving relief comprising a pressed powder formulation, the tablet being designed to disintegrate within a period of less than 60 seconds upon oral administration, the powder formulation comprising an amount of nicotine and a pH regulating agent.

22 Claims, No Drawings

(56) References Cited

OTHER PUBLICATIONS

"Crospovidone," 2006. Eds. Rowe et al. In Handbook of Pharmaceutical Excipients, Fifth Edition, Pharmaceutical Press. London, England. pp. 214-216, 26 pages.
"Crospovidone ED". Nov. 2002. In: Rowe RC, Sheskey PJ, Weller PJ, eds. Handbook of Pharmaceutical Excipients, Pharmaceutical Press, London, UK, p. 184, XP002719370. 2 pages.
Davies, "Oral Solid Dosage Forms," 2009. Ed. M. Gibson In Pharmaceutical Preformulation and Formulation, A Practical Guide from Candidate Drug Selection to Commercial Dosage Form, Second Edition, Chapter 11: Excerpt: pp. 397-399, 18 pages.
Deshmukh, "Mouth Dissolving Drug Delivery System: A Review," Jan. 2012. International Journal of PharmTech Research, 4(1): 412-421.
Dey et al., "Orodispersible tablets: A trend in drug delivery," Jul. 2010. Journal of Natural Science, Biology and Medicine, 1(1): 1-5.
Notice of Oppisition mailed May 11, 2022 in European Application No. 18821992.7, a foreign corresponding Application of U.S. Appl. No. 16/213,641, 3 pages.
European Office Action dated Mar. 3, 2021 in European Application No. 18821992.7, a foreign corresponding application of U.S. Appl. No. 16/213,641, 8 pages.
European Office Action dated Mar. 3, 2021 in European Application No. 18821993.5, a foreign corresponding application of U.S. Appl. No. 16/213,678, 9 pages.
European Search Report dated Sep. 14, 2021 in European Application No. 21182000.6, a foreign corresponding application of U.S. Appl. No. 16/213,641, 12 pages.
European Oral Summons dated Sep. 6, 2021 in European Application No. 18821993.5, a foreign corresponding application of U.S. Appl. No. 16/213,678, 17 pages.
"Guidance for Industry Oral Disintegrating Tablets," Dec. 2008. U.S. Department of Health and Human Services Food and Drug Administration Center for Drug Evaluation and Research, 6 pages.
Hickman, "Melt in the Mouth," Nov. 2017, The Medicine Maker, Discovery and Development, downloaded Jan. 14, 2023 from https://themedicinemaker.com/discovery-development/melt-in-the-mouth, 9 pages.
International Search Report and Written Opinion dated Mar. 14, 2019 in International Application No. PCT/DK2018/050338, 12 pages.
International Search Report and Written Opinion dated Mar. 14, 2019 in International Application No. PCT/DK2018/050339, 12 pages.
International Search Report and Written Opinion dated May 13, 2019 in International Application No. PCT/DK2018/050337, 15 pages.
Japanese Office Action dated Nov. 29, 2022 in Japanese Application No. JP2020-529346, a foreign corresponding application of U.S. Appl. No. 16/213,641, 8 pages.
"Kollidon® CL, Kollidon® CL-F, Kollidon® CL-SF, Kollidon® CL-M: Super-disintegrants and dissolution enhancers". Brochure from BASF The Chemical Company. www.pharma-solutions.basf.com, downloaded at least by May 11, 2022. 18 pages.
Laffleur, et. al., "Comprehensive mucoadhesive study of anionic polymers and their derivative", European Polymer Journal, vol. 93, Aug. 2017, pp. 314-322.
"Ludiflash® The taste of sucess: Making tablets as smooth as ice cream". Brochure from BASF The Chemical Company. www.pharma-ingredients.basf.com, downloaded at least by May 11, 2022. 12 pages.
"Mannitol" Jan. 2006. In: Rowe RC, Sheskey PJ, Weller PJ, eds. Handbook of Pharmaceutical Excipients, Pharmaceutical Press, London, UK, pp. 449-453, XP002537758 5 pages.
"Mannitol," 2006. Eds. Rowe et al. In Handbook of Pharmaceutical Excipients, Fifth Edition, Pharmaceutical Press. London, England. pp. 449-454, 28 pages.
Patil et al., "A Review on Mouth Dissolving Tablet," 2017. Journal of Applied Pharmaceutical Research, 5(2): 9-15.
Russian Office Action dated Dec. 17, 2021 in Russian Application No. 2020122405/04(038512), a foreign corresponding application of U.S. Appl. No. 16/213,641, 5 pages.
Shahab et al., "Novel Delivery Systems for Nicotine Replacement Therapy as an Aid to Smoking Cessation and for Harm Reduction: Rationale, and Evidence for Advantages over Existing Systems," CNS Drugs (2013) 27:1007-1019.
Tillotson, "Comparison of Directly Compressible Drug Delivery Systems for Orally Disintegrating Tablets," 2014. SPI Pharma, 2 pages.

NICOTINE TABLET

CROSS REFERENCE TO RELATED APPLICATIONS

This application is a continuation of co-pending U.S. patent application Ser. No. 16/213,641, filed Dec. 7, 2018, which claims priority to Danish Patent Application No. PA 2017 70925, filed Dec. 8, 2017, which are incorporated herein by reference in their entirety.

FIELD OF THE INVENTION

The present invention relates to the field of fast disintegrating tablets. In particular, the present invention pertains to formulations and methods used to employ nicotine more efficiently from fast disintegrating tablets applied orally by the sublingual or buccal route.

BACKGROUND OF THE INVENTION

Nicotine-releasing tablets applied for the purpose of providing a release of nicotine in a user's mouth over a certain period is well-known. Much effort has in prior art been put into emulating the nicotine release and oral perception of a cigarette when it is smoked by a user, which means that release profiles from nicotine tablets have been thoroughly investigated in prior art.

It is however an established fact that the one-to-one smoking-emulation is yet to be achieved with other means than a cigarette.

SUMMARY

The invention relates to an orally disintegrating nicotine tablet for nicotine craving relief comprising a pressed powder formulation, the tablet being designed to disintegrate within a period of less than 60 seconds upon oral administration, the powder formulation comprising an amount of nicotine and a pH regulating agent.

One advantage of the invention may be that effective nicotine craving relief is obtained while at the same time minimizing burning in the throat. A significant challenge with oral administration of nicotine is that it often leads to a very unpleasant burning sensation in the throat. This burning sensation is normally worsened when increasing the release rate of nicotine. Thus, obtaining effective nicotine craving relief and also at the same time minimizing burning in the throat is highly surprising.

One advantage of the invention may be that by obtaining a very fast disintegration of the tablet within a period of less than 60 seconds upon oral administration, and thereby facilitating fast release of nicotine together with pH regulating agent, a high concentration of nicotine combined with optimized pH is achieved in the oral cavity.

Furthermore, by ensuring the very fast disintegration of the table as described above, the tablet facilitates user compliance with instructions, such as not swallowing or spitting within a given time period from oral administration. When delivering nicotine slowly to the oral cavity, the user will eventually have to spit or swallow due to saliva generation, and may thus swallow or spit out unabsorbed nicotine, which is thus wasted. By keeping the period for disintegration very short and below 60 seconds upon oral administration, a very high concentration of nicotine and optimized pH may be obtained for a relatively long period before the user swallows or spits out.

A further advantage of the invention may be that the above described facilitation of high nicotine concentration and optimized pH may be concentrated locally in the oral cavity, such as sublingually, can facilitate absorption of nicotine into the bloodstream even further.

Contrary to expectations, experiments have shown that the permeability of nicotine across the buccal mucosa decreases relatively little when increasing the concentration of nicotine. For example, experiments have shown that an increase in the concentration of nicotine from 100 microgram/mL to 14,000 microgram/mL results in a decrease of about a factor of two. This is highly surprising and is utilized by aiming for concentrations of nicotine in the oral cavity, which are much higher than previously seen or desired. The present delivery vehicle thus benefits and aims for very high nicotine content in the oral cavity, thereby increasing the nicotine uptake. Furthermore, it has been realized that the effect of nicotine concentrations is thus at least comparable to the effect of pH regulation in the oral cavity. This is contrary to any expectations.

The meaning of being designed to disintegrate upon oral administration is that the tablet due to reaction with saliva already in the mouth and saliva optionally generated as a response to the inserted tablet as such when inserted into the mouth will disintegrate as a tablet. Such tablet may e.g. be referred to within the art as an orally disintegrating tablet (ODT: orally disintegrating tablet). Here the meaning of being disintegrated is the process where the oral dosage form falls apart or disintegrates in to smaller aggregates and as defined by European Pharmacopeia 2.9.1 "Disintegration of tablets and capsules". The time period of obtaining the desired disintegration, here less than 60 seconds, may be designed through use of materials such as polyols or binders known within the art. The tablet disintegration time should also consider the tablet manufacturing process, as a e.g. pressure force may influence how disintegrable the tablet may end up being when finalized. For specific tablets, a number of parameters is to be considered, hereunder composition and content of individual ingredients, hereunder amount and form of nicotine, amount and form of disintegrant pressure force used, type of orally disintegrating nicotine tablet, intended use of the orally disintegrating nicotine tablet, etc. The present application gives directions in the examples for the skilled person.

In an embodiment of the invention, the tablet is designed to disintegrate within a period of between 2 and 60 seconds upon oral administration, such as between 5 and 60 seconds upon oral administration, such as between 10 and 60 second upon oral administration.

In an embodiment of the invention, the tablet is designed to disintegrate within a period of less than 45 seconds upon oral administration.

In an embodiment of the invention, the tablet is designed to disintegrate within a period of between 2 and 45 seconds upon oral administration, such as between 5 and seconds upon oral administration, such as between 10 and 45 second upon oral administration.

In an embodiment of the invention, the tablet is designed to disintegrate within a period of less than 30 seconds upon oral administration.

In an embodiment of the invention, the tablet is designed to disintegrate within a period of between 2 and 30 seconds upon oral administration, such as between 5 and seconds upon oral administration, such as between 10 and 30 second upon oral administration.

In an embodiment of the invention, the tablet is designed to disintegrate within a period of less than 20 seconds upon oral administration, such as between 2 and 20 seconds upon oral administration, such as between 5 and 20 seconds upon oral administration, such as between 10 and 20 second upon oral administration.

In an embodiment of the invention, the tablet is designed to disintegrate within a period of less than 15 seconds upon oral administration, such as between 2 and 15 seconds upon oral administration, such as between 5 and 15 seconds upon oral administration, such as between 10 and 15 second upon oral administration.

In an embodiment of the invention, the tablet is designed to disintegrate within a period of between 10 and 25 seconds upon oral administration.

In an embodiment of the invention, the tablet is designed to disintegrate within a period of between 20 and 40 seconds upon oral administration.

In an embodiment of the invention, the tablet is designed to disintegrate within a period of between 20 and 60 seconds upon oral administration.

In an embodiment of the invention, the tablet is designed to disintegrate within a period of between 30 and 60 seconds upon oral administration.

In an embodiment of the invention, the tablet is designed for the content of nicotine to dissolve in the saliva within a period of less than 90 seconds upon oral administration.

In the present context dissolving of nicotine has meaning that it designates that nicotine upon the disintegration of the tablet is dissolved and thereby available for transport through the mucosa into the blood stream.

It should be noted that the period of 90 seconds of dissolving of the nicotine upon oral administration reflects that nicotine may dissolve slower than the tablet disintegrates. First of all, it should be noted that disintegration of the tablet may still involve the presence of smaller parts of the tablet and at least that some of the powder particles are not yet dissolved.

When using nicotine salt(s) as a source of nicotine, it should also be noted that nicotine salts are not necessarily dissolvable in water and thereby in the saliva. It may therefore be preferred to apply water-dissolvable nicotine salts within the scope of the invention.

In an embodiment of the invention, the tablet is designed for the content of nicotine to dissolve in the saliva within a period of less than 60 seconds upon oral administration.

In an embodiment of the invention, the tablet is designed for the content of nicotine to dissolve in the saliva within a period of less than 45 seconds upon oral administration.

In an embodiment of the invention, the tablet comprises nicotine in an amount of at least 0.5 mg.

In an embodiment of the invention, the tablet comprises nicotine in an amount of between 0.5 mg to 4 mg.

In an embodiment of the invention, nicotine is provided as a nicotine salt.

When applying a nicotine salt in the tablet, the resulting amount of nicotine salt needed to obtain e.g. 1 mg nicotine will be higher, depending on the specific salt, which is why the tablet will be loaded with an amount of nicotine salt corresponding to the desired amount of effective nicotine. For example, when using nicotine bitartrate (not hydrated form), the amount of nicotine bitartrate (not hydrated) needed to obtain 1 mg nicotine is about 2.8 mg.

In an embodiment of the invention, nicotine salt is a water-soluble nicotine salt.

The use of a nicotine salt in the present context is to obtain a nicotine presence in the nicotine disintegrable tablet, which is suitable as a relatively stable compound in the tablet, but also optimized for fast dissolving in the oral cavity.

In the present context, the term "water-soluble salt" is understood as a salt having a solubility in water of at least 10 g of salt per 100 mL water at standard lab conditions, including temperature of 25 degrees Celsius, atmospheric pressure, and pH of 7.

In an embodiment of the invention, the nicotine salt is selected from nicotine ascorbate, nicotine aspartate, nicotine benzoate, nicotine monotartrate, nicotine bitartrate, nicotine chloride (e.g., nicotine hydrochloride and nicotine dihydrochloride), nicotine citrate, nicotine fumarate, nicotine gensitate, nicotine lactate, nicotine mucate, nicotine laurate, nicotine levulinate, nicotine malate nicotine perchlorate, nicotine pyruvate, nicotine salicylate, nicotine sorbate, nicotine succinate, nicotine zinc chloride, nicotine sulfate, nicotine tosylate and nicotine salt hydrates (e.g., nicotine zinc chloride monohydrate).

In an embodiment of the invention, the nicotine salt is nicotine bitartrate.

In the present context, nicotine bitartrate includes hydrates thereof.

A specifically suitable nicotine salt applicable within the scope of the invention is nicotine bitartrate. If using nicotine bitartrate (not hydrated), the preferred amount would be about 1.4 to 11.6 mg as this would result in an effective amount of no more than 0.5 to 4 mg of nicotine in the saliva.

In an embodiment of the invention, nicotine is selected from the group consisting of a nicotine salt, the free base form of nicotine, a nicotine derivative, such as a nicotine cation exchanger, such as nicotine polacrilex resin, a nicotine inclusion complex or nicotine in any non-covalent binding; nicotine bound to zeolites; nicotine bound to cellulose, such as microcrystalline, or starch microspheres, and mixtures thereof.

In an embodiment of the invention said nicotine is provided as a synthetic nicotine.

An advantage of the above embodiment may be that a more desirable taste profile may be obtained by avoiding undesirable taste notes that may be included in nicotine obtained from tobacco.

In an embodiment of the invention said nicotine is provided as a complex between nicotine and an ion exchange resin.

In an embodiment of the invention said complex between nicotine and the ion exchange resin is nicotine polacrilex resin (NPR).

In an embodiment of the invention, the nicotine is provided in association with a fatty acid.

In an embodiment of the invention, the fatty acid is oleic acid.

In an embodiment of the invention, the nicotine is provided in ionic complex with at least one mucoadhesive water-soluble anionic polymer.

In an embodiment of the invention, the tablet is a sublingual tablet.

When the tablet is a sublingual tablet and when the tablet is used as a sublingual tablet, the transfer of nicotine in the mucosa is technically extremely advantageous in the sense that even the release rates obtained through the use of the disintegrable tablet results in a very high transfer of nicotine while affecting the user with much less burning than should be expected or which has been experienced in any prior art nicotine-delivering tablet. This effect is believed to be due to the fact that burning in the throat affects the user much stronger and maintains its effect over a longer period of time than when the nicotine is focused on sub-lingual transfer. This is even more advantageous, given the fact that very high concentrations of nicotine may be obtained sublingually with only minimum burning in the throat. A very high sublingually uptake thus both keeps the burning at a minimum and increases the nicotine uptake at the same time.

This burning sensation may e.g. be controlled or even reduced when applying the nicotine in the tablet in the form as a nicotine salt in an amount of 0.5 mg to 50 mg. The amount of nicotine salt should correspond to an amount of nicotine between 0.5 and 4 mg. The amount of nicotine salt will therefore depend on the specific nicotine salt applied.

In an embodiment of the invention, the pressed powder comprises at least one polyol and wherein the polyol comprises more than 40% by weight of the tablet.

In an embodiment of the invention, the tablet is pressed at a pressure of 2-20 kN.

According to an embodiment of the invention, the tablet is pressed at a pressure of 4-20 kN.

In an embodiment of the invention, the formulation provides a peak saliva concentration of nicotine of more than 0.3 mg/mL and a peak saliva pH of more than 8 during the first 120 seconds upon oral administration.

In an embodiment of the invention, the formulation provides a peak saliva concentration of nicotine of more than 0.4 mg/mL and a peak saliva pH of more than 8 during the first 120 seconds upon oral administration.

In an embodiment of the invention, the formulation provides a peak saliva concentration of nicotine of more than 0.5 mg/mL and a peak saliva pH of more than 8 during the first 120 seconds upon oral administration.

In embodiments where the formulation provides a peak saliva concentration of nicotine of more than 0.3 mg/mL during the first 120 seconds upon oral administration, the amount of nicotine in the tablet should be adjusted to at least the amount necessary for obtaining this. Depending on the specific formulation, the amount of nicotine in the tablet may be higher than 0.5 mg in some embodiments, such as e.g. at least 1 mg or at least 2 mg.

In embodiments where the formulation provides a peak saliva concentration of nicotine of more than 0.5 mg/mL during the first 120 seconds upon oral administration, the amount of nicotine in the tablet should be adjusted to at least the amount necessary for obtaining this. Depending on the specific formulation, the amount of nicotine in the tablet may be higher than 0.5 mg in some embodiments, such as e.g. at least 1 mg or at least 2 mg.

In an embodiment of the invention, the formulation is designed for the content of nicotine to dissolve in the oral saliva within a period of less than 90 seconds upon oral administration, and wherein at least 40% by weight of the nicotine is absorbed through the oral mucosa.

In an embodiment of the invention, the formulation is designed for the content of nicotine to dissolve in the oral saliva within a period of less than 90 seconds upon oral administration, and wherein at least 50% by weight of the nicotine is absorbed through the oral mucosa.

In an embodiment of the invention, the tablet further comprises a disintegrant.

One advantage of the above embodiment may be that said disintegrant facilitates the disintegration and dissolution of the tablet, whereby a release of the nicotine and pH controlling agent is achieved.

In an embodiment of the invention, the disintegrant is selected from starch, pregelatinated starch, modified starch (including potato starch, maize starch, starch 1500, sodium starch glycolate and starch derivatives), cellulose, microcrystalline cellulose, alginates, ion-exchange resin, and superdisintegrants, such as crosslinked cellulose (such as sodium carboxy methyl cellulose), crosslinked polyvinyl pyrrolidone (PVP), crosslinked starch, crosslinked alginic acid, natural superdisintegrants, and calcium silicate, and combinations thereof.

In an embodiment of the invention the disintegrant comprises cross-linked polyvinylpyrrolidone.

In an embodiment of the invention the disintegrant is cross-linked polyvinylpyrrolidone.

An advantage of using cross-linked polyvinylpyrrolidone, also known as crospovidone, as disintegrant, may be that it decreases the dependence of the disintegration time on the compression force while allowing rather low disintegration times. This may be very preferred especially for fast disintegrating tablets. Also, by being more independent from compression force, a lower variation between tablets due to variations in compression force is facilitated.

In an embodiment of the invention at least 50% by weight of the cross-linked polyvinylpyrrolidone has a particle size below 50 micrometers.

This corresponds to commercial grades CL-F and CL-SF.

In an embodiment of the invention at least 25% by weight of the cross-linked polyvinylpyrrolidone has a particle size below 15 micrometers.

This corresponds to commercial grade CL-SF.

An advantage of the above embodiment of using cross-linked polyvinylpyrrolidone with a smaller particle size facilitates a shorter disintegration time, e.g. due to a larger relative surface of the disintegrant particles.

In an embodiment of the invention the tablet comprises disintegrant in an amount of 1-10% by weight of the tablet.

According to an embodiment of the invention, the tablet comprises disintegrant in an amount of 2-8% by weight of the tablet, such as 4-6% by weight of the tablet, such as about 5% by weight of the tablet.

Advantageously, the level of disintegrant is high enough to obtain a fast disintegration, but not too high as high amounts may increase production costs unnecessarily.

In an embodiment of the invention the tablet comprises sodium stearyl fumarate (SSF) as a lubricant.

An advantage of the above embodiment may be that it facilitates a shorter disintegration time of the tablet.

In an embodiment of the invention, the tablet comprises pH regulating agent in an amount of at least 2.7 percent by weight of said tablet.

According to an embodiment of the invention, the tablet comprises said pH regulating agent in an amount of between 2.7 and 5.7% by weight of said tablet.

In an embodiment of the invention, the tablet has a weight of 25 to 200 mg, such as 50 to 150 mg, such as 70-120 mg, such as about 75 mg or about 100 mg.

An advantage of the above embodiment may be that it provides a desirable low disintegration time, while allowing a sufficiently high nicotine amount to be included in the tablet.

In an embodiment of the invention, the tablet comprises microcrystalline cellulose in an amount of 1-10% by weight of the tablet.

An advantage of the above embodiment is that a lower friability may be obtained without compromising the mouthfeel. Including too high amounts of microcrystalline cellulose may lead to a dusty mouthfeel.

According to an embodiment of the invention, the tablet comprises microcrystalline cellulose in an amount of 2-8% by weight of the tablet, such as 4-6% by weight of the tablet, such as about 5% by weight of the tablet.

In an embodiment of the invention, the tablet comprises mannitol as a bulk sweetener.

Using mannitol is advantageous due to a lower compactability compared to e.g. sorbitol, isomalt, and xylitol, i.e. for a given compression force a lower hardness of the tablet is obtained by using mannitol compared to sorbitol, isomalt or xylitol.

In an embodiment of the invention, the tablet comprises a pressed powder formulation, the tablet being designed to disintegrate within a period of less than 60 seconds upon oral administration, the powder formulation comprising an amount of nicotine salt and a pH regulating agent and wherein the tablet is designed for the content of nicotine to dissolve in the saliva within a period of less than 90 seconds upon oral administration.

In an embodiment of the invention, the tablet comprises a pressed powder formulation, the tablet being designed to disintegrate within a period of less than 60 seconds upon oral administration, the powder formulation comprising an amount of nicotine salt and a pH regulating agent and wherein the tablet is designed for the content of nicotine to dissolve within a period of less than 90 seconds upon oral administration and wherein the nicotine salt is water soluble.

The invention further relates to an orally disintegrating nicotine tablet for use in the alleviation of nicotine craving, comprising a pressed powder formulation, the tablet being designed to disintegrate within a period of less than 60 seconds upon oral administration, the powder formulation comprising an amount of nicotine and a pH regulating agent.

In the present context, it should be understood that said use in the alleviation of nicotine craving involves administering said orally disintegrating nicotine tablet orally.

In an embodiment of the invention, the orally disintegrating nicotine tablet comprises a pressed powder formulation, the tablet being designed to disintegrate within a period of less than 60 seconds upon oral administration, the powder formulation comprising an amount of nicotine salt and a pH regulating agent, wherein the tablet wherein the tablet is designed for the content of nicotine to dissolve within a period of less than 90 seconds upon oral administration.

In an embodiment of the invention the nicotine is not in ionic complex with a mucoadhesive water-soluble anionic polymer.

In an embodiment of the invention the nicotine does not contain a nicotine complex.

According to an embodiment of the invention, the orally disintegrating nicotine tablet for nicotine craving relief comprises a pressed powder formulation, the tablet being designed to disintegrate within a period of less than 60 seconds upon oral administration, the powder formulation comprising an amount of nicotine and a pH regulating agent, and wherein the tablet is designed for the content of nicotine to dissolve in the saliva within a period of less than 90 seconds upon oral administration.

According to an embodiment of the invention, the orally disintegrating nicotine tablet for nicotine craving relief comprises a pressed powder formulation, the tablet being designed to disintegrate within a period of less than 60 seconds upon oral administration, the powder formulation comprising an amount of nicotine and a pH regulating agent, wherein the tablet is designed for the content of nicotine to dissolve in the saliva within a period of less than 90 seconds upon oral administration and wherein the nicotine is provided as a nicotine salt. This salt should preferably be a water-soluble salt.

In an embodiment of the invention, the orally disintegrating nicotine tablet comprises a pressed powder formulation, the tablet being designed to disintegrate within a period of less than 60 seconds upon oral administration, the powder formulation comprising an amount of nicotine salt and a pH regulating agent, wherein the tablet wherein the tablet is designed for the content of nicotine to dissolve within a period of less than 90 seconds upon oral administration and wherein the tablet comprises nicotine in an amount of between 0.5 mg to 4 mg.

In an embodiment of the invention, the orally disintegrating nicotine tablet comprises a pressed powder formulation, the tablet being designed to disintegrate within a period of less than 60 seconds upon oral administration, the powder formulation comprising an amount of nicotine salt and a pH regulating agent, wherein the tablet wherein the tablet is designed for the content of nicotine to dissolve within a period of less than 90 seconds upon oral administration, wherein the tablet comprises nicotine in an amount of between 0.5 mg to 4 mg administration and wherein the nicotine is provided as a nicotine salt. This salt should preferably be a water-soluble salt.

According to an embodiment of the invention, the orally disintegrating nicotine sublingual tablet for nicotine craving relief comprises a pressed powder formulation, the tablet being designed to disintegrate within a period of less than 60 seconds upon oral administration, the powder formulation comprising an amount of nicotine and a pH regulating agent, and wherein the tablet is designed for the content of nicotine to dissolve in the saliva within a period of less than 90 seconds upon oral administration.

According to an embodiment of the invention, the orally disintegrating nicotine sublingual tablet for nicotine craving relief comprises a pressed powder formulation, the tablet being designed to disintegrate within a period of less than 60 seconds upon oral administration, the powder formulation comprising an amount of nicotine and a pH regulating agent, wherein the tablet is designed for the content of nicotine to dissolve in the saliva within a period of less than 90 seconds upon oral administration and wherein the nicotine is provided as a nicotine salt. This salt should preferably be a water-soluble salt.

In an embodiment of the invention, the orally disintegrating sublingual nicotine tablet comprises a pressed powder formulation, the tablet being designed to disintegrate within a period of less than 60 seconds upon oral administration, the powder formulation comprising an amount of nicotine salt and a pH regulating agent, wherein the tablet wherein the tablet is designed for the content of nicotine to dissolve within a period of less than 90 seconds upon oral administration and wherein the tablet comprises nicotine in an amount of between 0.5 mg to 4 mg.

In an embodiment of the invention, the orally disintegrating sublingual nicotine tablet comprises a pressed powder formulation, the tablet being designed to disintegrate within a period of less than 60 seconds upon oral administration, the powder formulation comprising an amount of nicotine salt and a pH regulating agent, wherein the tablet wherein the tablet is designed for the content of nicotine to dissolve within a period of less than 90 seconds upon oral administration, wherein the tablet comprises nicotine in an amount of between 0.5 mg to 4 mg administration and wherein the nicotine is provided as a nicotine salt. This salt should preferably be a water-soluble salt.

According to an embodiment of the invention, the orally disintegrating nicotine tablet for nicotine craving relief comprises a pressed powder formulation, the tablet being designed to disintegrate within a period of less than 60 seconds upon oral administration, the powder formulation comprising an amount of nicotine and a pH regulating agent, and wherein the tablet is designed for the content of nicotine to dissolve in the saliva within a period of less than 90 seconds upon oral administration and wherein the pressed powder comprises at least one polyol and wherein the polyol comprises more than 40% by weight of the tablet.

According to an embodiment of the invention, the orally disintegrating nicotine tablet for nicotine craving relief comprises a pressed powder formulation, the tablet being designed to disintegrate within a period of less than 60 seconds upon oral administration, the powder formulation comprising an amount of nicotine and a pH regulating agent, wherein the tablet is designed for the content of nicotine to dissolve in the saliva within a period of less than 90 seconds upon oral administration, wherein the pressed powder comprises at least one polyol and wherein the polyol comprises more than 40% by weight of the tablet and wherein the nicotine is provided as a nicotine salt. This salt should preferably be a water-soluble salt.

In an embodiment of the invention, the orally disintegrating nicotine tablet comprises a pressed powder formulation, the tablet being designed to disintegrate within a period of less than 60 seconds upon oral administration, the powder formulation comprising an amount of nicotine salt and a pH regulating agent, wherein the tablet wherein the tablet is designed for the content of nicotine to dissolve within a period of less than 90 seconds upon oral administration, wherein the pressed powder comprises at least one polyol and wherein the polyol comprises more than 40% by weight of the tablet and wherein the tablet comprises nicotine in an amount of between 0.5 mg to 4 mg.

In an embodiment of the invention, the orally disintegrating nicotine tablet comprises a pressed powder formulation, the tablet being designed to disintegrate within a period of less than 60 seconds upon oral administration, the powder formulation comprising an amount of nicotine salt and a pH regulating agent, wherein the tablet wherein the tablet is designed for the content of nicotine to dissolve within a period of less than 90 seconds upon oral administration, wherein the pressed powder comprises at least one polyol and wherein the polyol comprises more than 40% by weight of the tablet and wherein the tablet comprises nicotine in an amount of between 0.5 mg to 4 mg administration and wherein the nicotine is provided as a nicotine salt. This salt should preferably be a water-soluble salt.

Moreover the invention relates to a method of alleviation of nicotine craving by administering an effective amount of said orally disintegrating nicotine tablet according to the invention or any of its embodiments.

DETAILED DESCRIPTION

As used herein, the term "orally disintegrating tablet" refers to a tablet for oral administering which disintegrates in the oral cavity relatively fast from the administering, such as within about three minutes from oral administering. Orally disintegrating tablets may be intended for use as a sublingual tablet for positioning under the tongue, as a buccal tablet, as a tablet for melting on the tongue, or for other types of oral administering.

Orally disintegrating tablets may also be referred to "orally dissolving tablets", and these two terms are used interchangeably herein. Commonly, these terms are also referred to by their abbreviation, ODT. Similarly, the terms "fast dissolving tablet" and "fast disintegrating tablet", as well as the abbreviation FDT, refers herein to an orally disintegrating tablet.

As used herein, the term "disintegrate" refers to a reduction of a said object to components, fragments or particles. Disintegration time is measured in vitro. The in vitro measurements are carried out in accordance to European Pharmacopeia 9.0, section 2.9.1, Disintegration of tablets and capsules.

As used herein, the term "dissolve" is the process where a solid substance enters a solvent (oral saliva) to yield a solution. Unless otherwise stated, dissolving implies a full dissolving of the compound in question.

As used herein, the terms "disintegrant" refers to an ingredient facilitating disintegration of an orally disintegrating tablet, when the orally disintegrating tablet comes into contact with saliva. Disintegrants usable within the scope of the invention may include starch, pregelatinated starch, modified starch (including potato starch, maize starch, starch 1500, sodium starch glycolate and starch derivatives), cellulose, microcrystalline cellulose, alginates, ion-exchange resin, and superdisintegrants, such as crosslinked cellulose (such as sodium carboxy methyl cellulose), crosslinked polyvinyl pyrrolidone (PVP), crosslinked starch, crosslinked alginic acid, natural superdisintegrants, and calcium silicate. Disintegrants may often be considered as measure promoting the break-up of the dosage form into smaller fragments upon administration to allow the onset of drug dissolution and eventual absorption.

As used herein, the term "nicotine" refers to nicotine in any form, including free base nicotine, nicotine salts, nicotine bound to ion exchange resins, such as nicotine polacrilex, nicotine bound to zeolites; nicotine bound to cellulose, such as microcrystalline cellulose, such as of microbial origin, or starch microspheres, nicotine bound to CaCO3, and mixtures thereof. Thus, when referring to nicotine amounts, the amounts refers to the amount of pure nicotine. Thus, when measuring the concentration of nicotine added as nicotine salt, it is the mass of the equivalent amount of pure nicotine, not the mass of the salt, that is relevant. Nicotine also covers nicotine not obtained from tobacco, often referred to as synthetic nicotine.

As used herein, the term "nicotine salt" refers to nicotine in ionized form bonded electrostatically to a counterion.

As used herein, the term "NBT" refers to nicotine bitartrate and hydrates thereof.

As used herein, the term "%" and "percent" refers to percent by weight, unless otherwise is stated.

As used herein, the term "release of nicotine" refers to the nicotine being made bioavailable, i.e. available for absorption over the mucous membrane in the oral cavity. While some forms of nicotine require dissolution for being bioavailable, other forms may be readily absorbed into the body without dissolution. For example, in order for the nicotine to be bioavailable, the matrix of the solid formulation should be disintegrated. Some forms of nicotine require the nicotine to further be released from e.g. a carrier, e.g. nicotine from a nicotine-ion exchange resin such as nicotine polacrilex. Other nicotine forms, such nicotine salts, hereunder nicotine bitartrate, may readily dissolve upon disintegration of the matrix of the solid formulation. Still, some nicotine forms may not require dissolving. This applies for e.g. nicotine free base, which is released upon disintegration of the solid formulation matrix.

As used herein, the term "peak saliva concentration of nicotine" refers to the peak value of the concentration of nicotine in saliva of the oral cavity, where the saliva includes delivery vehicle of the nicotine dissolved therein. Also, it should be understood that the peak saliva concentration is considered to be achieved whenever the criterion is fulfilled.

E.g. if a peak saliva concentration of nicotine is at least 0.5 mg/mL, this peak saliva concentration is achieved whenever the concentration of nicotine exceeds 0.5 mg/mL. Measurements of peak saliva nicotine concentration is performed as follows:

One dosage of the tablet is administered sublingually to at least six individuals. At specified time intervals, the saliva is collected. The experiment is repeated. Thus, each nicotine concentration value is the arithmetic mean of 12 measurements, i.e. performed on saliva-samples from six individuals times 2. The nicotine concentration of saliva is analyzed on HPLC after extraction into relevant buffer.

As used herein, the term "peak saliva pH" refers to the peak value of the pH in saliva of the oral cavity, where the saliva includes any delivery vehicle of the pH regulating agent. Also, it should be understood that the peak saliva pH is considered to be achieved whenever the criterion is fulfilled. E.g. if a peak saliva pH is at least 7.5, this peak saliva pH is achieved whenever the pH exceeds 7.5. Peak saliva pH is measured in vivo and is measured as follows:

At least 6 individuals chewed on a gum base free of buffer for 1 minute, after which the initial pH in a sample from the saliva from each of the individuals is measured with a suitable pH-electrode system, e.g. a stainless steel electrode PHW77-SS. Only individuals having, after chewing on a gum base free of buffer for one minute, an initial pH in the saliva inside the range from 6.7 and 7.3 are selected. These individuals thereby qualify as average individuals.

One dosage of the tablet is administered sublingually to at least six individuals. Hereafter, the saliva pH from each of the six individuals is measured at specified time intervals. Thus, each pH-value is the arithmetic mean of six measurements performed on saliva-samples from six individuals.

As used herein, the term "pH regulating agent" refers to agents, which active adjust and regulates the pH value of the solution to which they have been added or are to be added. Thus, pH regulating agents may be acids and bases, including acidic buffering agents and alkaline buffering agents. On the other hand, pH regulating agents does not including substances and compositions that can only affect the pH by dilution. Furthermore, pH regulating agents does not include e.g. flavoring, fillers, etc.

As used herein, the term "buffering agent" is used interchangeably with "buffer" and refers to agents for obtaining a buffer solution. Buffering agents include acidic buffering agents, i.e. for obtaining a buffer solution with an acidic pH, and alkaline buffering agents, i.e. for obtaining a buffer solution with an alkaline pH.

As used herein, the term "fast onset nicotine craving relief" refers to relief of nicotine craving, for which the onset is relatively fast, i.e. only a relatively short period of time after oral administering. In embodiments of the invention, the fast onset refers to a period after oral administration until craving relief is experienced being no more than 180 seconds, such as no more than 120 seconds, such as no more than 60 seconds.

EXAMPLES

The following non-limiting examples illustrate different variations of the present invention.

Example 1

Preparation of Fast Disintegrating Tablet

In the present example six fast disintegrating tablets (FDT) with 1 mg nicotine are prepared with formulations as outlined in table 1. The fast disintegrating tablet is prepared with NBT (nicotine bitartrate dihydrate). Punch used: 7.00 mm, circular, shallow concave, D tooling. Tablet weight: 100.0 mg.

TABLE 1

Fast disintegrating tablet compositions. Amounts are given in mg.

|  | FDT(a) | FDT(b) | FDT(c) | FDT(d) | FDT(e) | FDT(f) |
|---|---|---|---|---|---|---|
| NBT | 2.849 | 2.849 | 2.849 | 2.849 | 2.849 | 2.849 |
| Microcrystalline cellulose | — | — | — | 40.175 | 40.175 | 40.175 |
| Mannitol | 81.351 | 81.351 | 81.351 | 40.175 | 40.175 | 40.175 |
| Crospovidone | 5.0 | — | — | 5.0 | — | — |
| Croscarmellose Sodium | — | 5.0 | — | — | 5.0 | — |
| Sodium Starch Glycolate | — | — | 5.0 | — | — | 5.0 |
| Peppermint | 4.0 | 4.0 | 4.0 | 4.0 | 4.0 | 4.0 |
| Menthol | 0.4 | 0.4 | 0.4 | 0.4 | 0.4 | 0.4 |
| Sucralose | 0.4 | 0.4 | 0.4 | 0.4 | 0.4 | 0.4 |
| Sodium carbonate | 5.0 | 5.0 | 5.0 | 5.0 | 5.0 | 5.0 |
| Silicium dioxide | — | — | — | 1.0 | 1.0 | 1.0 |
| Magnesium stearate | 1.0 | 1.0 | 1.0 | 1.0 | 1.0 | 1.0 |
| Total | 100.0 | 100.0 | 100.0 | 100.0 | 100.0 | 100.0 |

FDT = Fast disintegrating tablet.

Raw materials are weighed from bags or buckets into separate weighing containers.

All excipients are sifted through an 800 micrometer sieve into a stainless steel or plastic bin in the following order:
Half the filler/bulk sweetener
The API and all other excipients, except magnesium stearate
The remaining half of the filler/bulk sweetener These are mixed in a Turbula mixer for 4-10 minutes at 25 RPM. Then lubricant, for example magnesium stearate is sifted through an 800 micrometer sieve into the mixing bin, and the lubrication is conducted by additional mixing for 1-2 minutes at 25 RPM. The fill level of the mixing bin is kept between 40% and 70%, according to standardized practice. The lubricated powder blend is transferred to the hopper of a tableting machine.

The fast disintegrating tablets are manufactured on a lab scale machine, for example RIVA Piccola bi-layer tablet press. The tablet machine is commissioned by adjusting the fill depth and compression force so the weight and hardness of lozenges match the acceptance criteria. A pre-compression force could be included to avoid capping.

TABLE 2

Suggested start up parameters.

| Parameter | Target value |
|---|---|
| Speed | 10-20 rpm |
| Weight of FDT | 100 mg +/− 5% |
| Compression force | 2-8 kN |
| Thickness | N/A* |
| Friability (100 rpm) | <1% |

*The design of punches is not fixed. As the curvature impacts thickness, the thickness is not a fixed target at this time of development.

The acceptance criteria for friability should be fulfilled so packaging of the resulting fast disintegrating tablets is possible, but in this embodiment, the bulk sweetener and or filler should have relatively good compressibility and still have fast disintegration. The fast disintegrating tablets according to the invention may comprise coloring agents. According to an embodiment of the invention, the fast disintegrating tablets may comprise color agents and whiteners such as FD&C-type dyes and lakes, fruit and vegetable extracts, titanium dioxide and combinations thereof.

Example 2

Preparation of Fast Disintegrating Tablet Using Ready to Use Systems

Another way of preparing fast disintegrating tablets would be to use a ready to use system. Suitable for the purpose could be but not limited to: Pearlitol Flash (Roquette), Pharmaburst 500 (SPI Pharma), Ludiflash (BASF), ProSolv (JRS Pharma), ProSolv EasyTab (JRS Pharma), F-Melt (Fuji Chemical), SmartEx50 or SmartEx100 (Shin Etsu/Harke Pharma). These ready to use systems co-processed systems where filler, disintegrant, glidant or similar are implemented in the one powder mix. This saves handling of several excipients and ensures homogeneity between excipients.

In the present example five fast disintegrating tablets (FDT(g)-FDT(k)) without nicotine are prepared with ready to use systems in formulations as outlined in table 3A. The fast disintegrating tablet is prepared without NBT (placebo). Adding nicotine to the fast disintegrating tablets is expected to influence disintegration time only insignificantly.

In this example, the following conditions where applied. Punch used: 7.00 mm, circular, shallow concave, B tooling. Tablet weight: 100.0 mg.

TABLE 3A

Fast disintegrating tablet compositions with different ready to use systems. Amounts are given in mg.

|  | FDT(g) | FDT(h) | FDT(i) | FDT(j) | FDT(k) |
| --- | --- | --- | --- | --- | --- |
| Ludiflash | 81.7 | — | — | — | — |
| Pearlitol Flash | — | 81.7 | — | — | — |
| SmartEx QD50 | — | — | 81.7 | — | — |
| F-Melt | — | — | — | 83.7 | — |
| ProSolv ODT G2 | — | — | — | — | 83.7 |
| Peppermint | 4.4 | 4.4 | 4.4 | 4.4 | 4.4 |
| Menthol | 1.5 | 1.5 | 1.5 | 1.5 | 1.5 |
| Sucralose | 0.4 | 0.4 | 0.4 | 0.4 | 0.4 |
| Sodium carbonate | 5.0 | 5.0 | 5.0 | 5.0 | 5.0 |
| Crospovidone | 5.0 | 5.0 | 5.0 | — | — |
| Croscarmellose Sodium | — | — | — | 3.0 | — |
| Sodium Starch Glycolate | — | — | — | — | 3.0 |
| Magnesium stearate | 2.0 | 2.0 | 2.0 | 2.0 | 2.0 |
| Total | 100.0 | 100.0 | 100.0 | 100.0 | 100.0 |

FDT = Fast disintegrating tablet.

Additionally, five fast disintegrating tables (FDT(1)-FDT(p)) with nicotine are prepared with ready to use systems in formulations as outlined in table 3B.

In this example, the following conditions where applied. Punch used: 7.00 mm, circular, shallow concave, B tooling. Tablet weight: 100.0 mg.

TABLE 3B

Fast disintegrating tablet compositions with different ready to use systems and nicotine as nicotine bitartrate, NBT or nicotine polacrilex, NPR (15% nicotine load). Amounts are given in mg.

|  | FDT(l) | FDT(m) | FDT(n) | FDT(o) | FDT(p) |
| --- | --- | --- | --- | --- | --- |
| NBT | — | — | 3.0 | 3.0 | 3.0 |
| NPR | 6.7 | 6.7 | — | — | — |
| Ludiflash | 75.0 | — | — | — | — |
| Pearlitol Flash | — | 75.0 | — | — | — |
| SmartEx QD50 | — | — | 78.7 | — | — |
| F-Melt | — | — | — | 80.7 | — |
| ProSolv ODT G2 | — | — | — | — | 80.7 |
| Peppermint | 4.4 | 4.4 | 4.4 | 4.4 | 4.4 |
| Menthol | 1.5 | 1.5 | 1.5 | 1.5 | 1.5 |
| Sucralose | 0.4 | 0.4 | 0.4 | 0.4 | 0.4 |
| Sodium carbonate | 5.0 | 5.0 | 5.0 | 5.0 | 5.0 |
| Crospovidone | 5.0 | 5.0 | 5.0 | — | — |
| Croscarmellose Sodium | — | — | — | 3.0 | — |
| Sodium Starch Glycolate | — | — | — | — | 3.0 |
| Magnesium stearate | 2.0 | 2.0 | 2.0 | 2.0 | 2.0 |
| Total | 100.0 | 100.0 | 100.0 | 100.0 | 100.0 |

FDT = Fast disintegrating tablet.

Further four fast disintegrating tablets (FDT(1)-FDT(4)) with nicotine are prepared with varying amounts of MCC (microcrystalline cellulose) as filler, as outlined in table 3C.

In this example, the following conditions where applied. Punch used: 7.00 mm, circular, shallow concave, B tooling. Tablet weight: 100.0 mg.

TABLE 3C

Fast disintegrating tablet compositions with varying amounts of MCC and nicotine (1 mg/tablet) sorbed onto calcium carbonate, (synthetic free nicotine base sorted onto calcium carbonate in a weight ratio of 1:2). Amounts are given in mg.

|  | FDT(1) | FDT(2) | FDT(3) | FDT(4) |
| --- | --- | --- | --- | --- |
| Nicotine-calcium carbonate | 3.0 | 3.0 | 3.0 | 3.0 |
| Microcrystalline cellulose | 0.0 | 5.0 | 10.0 | 20.0 |
| Mannitol | 79.7 | 74.7 | 69.7 | 59.7 |
| Crospovidone | 5.0 | 5.0 | 5.0 | 5.0 |
| Peppermint | 4.4 | 4.4 | 4.4 | 4.4 |
| Menthol | 1.5 | 1.5 | 1.5 | 1.5 |
| Sucralose | 0.4 | 0.4 | 0.4 | 0.4 |
| Sodium carbonate | 5.0 | 5.0 | 5.0 | 5.0 |
| Magnesium stearate | 1.0 | 1.0 | 1.0 | 1.0 |
| Total | 100.0 | 100.0 | 100.0 | 100.0 |

FDT = Fast disintegrating tablet.

Four fast disintegrating tablets, FDT(5)-FDT(8), with nicotine are prepared with varying amounts of disintegrant, as outlined in table 3D.

In this example, the following conditions where applied. Punch used: 7.00 mm, circular, shallow concave, B tooling. Tablet weight: 100.0 mg.

TABLE 3D

Fast disintegrating tablet compositions with varying amount of disintegrant. Amounts are given in mg.

|  | FDT(5) | FDT(6) | FDT(7) | FDT(8) |
| --- | --- | --- | --- | --- |
| NBT | 3.0 | 3.0 | 3.0 | 3.0 |
| Mannitol | 41.7 | 39.2 | 41.7 | 31.7 |
| Microcrystalline cellulose | 43 | 43 | 43 | 43 |
| Crospovidone | 0.0 | 2.5 | 5.0– | 10.0 |
| Peppermint | 4.4 | 4.4 | 4.4 | 4.4 |
| Menthol | 1.5 | 1.5 | 1.5 | 1.5 |
| Sucralose | 0.4 | 0.4 | 0.4 | 0.4 |

TABLE 3D-continued

Fast disintegrating tablet compositions with varying amount of disintegrant. Amounts are given in mg.

|  | FDT(5) | FDT(6) | FDT(7) | FDT(8) |
|---|---|---|---|---|
| Sodium carbonate | 5.0 | 5.0 | 5.0 | 5.0 |
| Magnesium stearate | 1.0 | 1.0 | 1.0 | 1.0 |
| Total | 100.0 | 100.0 | 100.0 | 100.0 |

FDT = Fast disintegrating tablet.

Three fast disintegrating tablets, FDT(9)-FDT(11), with nicotine are prepared with varying types of lubricants, as outlined in table 3E.

In this example, the following conditions where applied. Punch used: 7.00 mm, circular, shallow concave, B tooling. Tablet weight: 100.0 mg.

TABLE 3E

Fast disintegrating tablet compositions. Amounts are given in mg.

|  | FDT(9) | FDT(10) | FDT(11) |
|---|---|---|---|
| NBT | 3.0 | 3.0 | 3.0 |
| Microcrystalline cellulose | 5 | 5 | 5 |
| Mannitol | 78.6 | 77.6 | 77.6 |
| Crospovidone | 5.0 | 5.0 | 5.0 |
| Eucamenthol Flavour | 2 | 2 | 2 |
| Sucralose | 0.4 | 0.4 | 0.4 |
| Sodium carbonate | 5.0 | 5.0 | 5.0 |
| Magnesium stearate | 1.0 | — | — |
| Sodium stearyl fumarate | — | 2.0 | — |
| Compritol HD5 | — | — | 2.0 |
| Total | 100.0 | 100.0 | 100.0 |

FDT = Fast disintegrating tablet.

Three fast disintegrating tablets, FDT(12)-FDT(14), with nicotine are prepared, as outlined in table 3F.

In this example, the following conditions where applied. Punch used: 7.00 mm, circular, shallow concave, B tooling. Tablet weight: 75.0 mg.

TABLE 3F

Fast disintegrating tablet compositions. Amounts are given in mg. FDT = Fast disintegrating tablet. FDT(13) was made similar to FDT(12) but without buffer. FDT(14) was made similar to FDT(12) but without disintegrant.

|  | FDT(12) | FDT(13) | FDT(14) |
|---|---|---|---|
| SmartEx QD 50 | 60.0 | 65.0 | 65.0 |
| Nicotine Bitartrate (NBT) | 3.0 | 3.0 | 3.0 |
| Sodium carbonate anhydrous | 5.0 | 0.0 | 5.0 |
| Crospovidone (Kollidon CL-F, BASF) | 5.0 | 5.0 | 0.0 |
| Peppermint Powder | 0.4 | 0.4 | 0.4 |
| Sucralose | 0.4 | 0.4 | 0.4 |
| Aerosil 200 (silicium dioxide) | 0.2 | 0.2 | 0.2 |
| Magnesium Stearate | 1.0 | 1.0 | 1.0 |
| Total | 75.0 | 75.0 | 75.0 |

FDT(12)-FDT(13) were pressed to a hardness of 15-20 N. FDT (14) was pressed to a hardness of 25-35 N.

As described below, the tablets may be made from a wide range of different formulations.

As can be seen in table 1, microcrystalline cellulose is used as a filler. Lower amount of filler such as microcrystalline cellulose may also be used. Examples of usable fillers include magnesium- and calcium carbonate, sodium sulphate, ground limestone, silicate compounds such as magnesium- and aluminum silicate, kaolin and clay, aluminum oxide, silicium oxide, talc, titanium oxide, mono-, di- and tri-calcium phosphates, cellulose polymers, such as wood, starch polymers, fibers and combinations thereof.

As can be seen in table 1, mannitol is used as a bulk sweetener. Examples of usable bulk sweeteners include sugar sweetener and/or sugarless sweetener.

The bulk sweeteners may often support the flavor profile of the formulation.

Sugar sweeteners generally include, but are not limited to saccharide-containing components, such as sucrose, dextrose, maltose, saccharose, lactose, sorbose, dextrin, trehalose, D-tagatose, dried invert sugar, fructose, levulose, galactose, corn syrup solids, glucose syrup, hydrogenated glucose syrup, and the like, alone or in combination. These sugar sweeteners may also be included as a humectant.

Sugarless sweeteners generally include, but are not limited to sugar alcohols (also sometimes referred to as polyols) such as sorbitol, erythritol, xylitol, maltitol, mannitol, lactitol, and isomalt.

As can be seen in table 1 and 3A-3F, crospovidone, croscarmellose sodium, and sodium starch glycolate are used as disintegrants. Examples of usable disintegrants include starch, pregelatinated starch, modified starch (including potato starch, maize starch, starch 1500, sodium starch glycolate and starch derivatives), cellulose, microcrystalline cellulose, alginates, ion-exchange resin, and superdisintegrants, such as crosslinked cellulose (such as sodium carboxy methyl cellulose), crosslinked polyvinyl pyrrolidone (PVP), crosslinked starch, crosslinked alginic acid, natural superdisintegrants, and calcium silicate, and combinations thereof.

As can be seen in table 1 and 3A-3F, sucralose is used as a high intensity sweetener. Usable high intensity sweeteners include, but are not limited to sucralose, aspartame, salts of acesulfame, such as acesulfame potassium, alitame, saccharin and its salts, cyclamic acid and its salts, glycyrrhizin, dihydrochalcones, thaumatin, monellin, stevioside and the like, alone or in combination.

As can be seen in table 1 and 3A-3F, peppermint and menthol are used as flavors. Usable flavors include almond, almond amaretto, apple, Bavarian cream, black cherry, black sesame seed, blueberry, brown sugar, bubblegum, butterscotch, cappuccino, caramel, caramel cappuccino, cheesecake (graham crust), cinnamon redhots, cotton candy, circus cotton candy, clove, coconut, coffee, clear coffee, double chocolate, energy cow, graham cracker, grape juice, green apple, Hawaiian punch, honey, Jamaican rum, Kentucky bourbon, kiwi, koolada, lemon, lemon lime, tobacco, maple syrup, maraschino cherry, marshmallow, menthol, milk chocolate, mocha, Mountain Dew, peanut butter, pecan, peppermint, raspberry, banana, ripe banana, root beer, RY 4, spearmint, strawberry, sweet cream, sweet tarts, sweetener, toasted almond, tobacco, tobacco blend, vanilla bean ice cream, vanilla cupcake, vanilla swirl, vanillin, waffle, Belgian waffle, watermelon, whipped cream, white chocolate, wintergreen, amaretto, banana cream, black walnut, blackberry, butter, butter rum, cherry, chocolate hazelnut, cinnamon roll, cola, creme de menthe, eggnog, English toffee, guava, lemonade, licorice, maple, mint chocolate chip, orange cream, peach, pina colada, pineapple, plum, pomegranate, pralines and cream, red licorice, salt water taffy, strawberry banana, strawberry kiwi, tropical punch, tutti frutti, vanilla, or any combination thereof.

According to an embodiment of the invention, flavor may be used as taste masking for the nicotine.

In some embodiments of the invention, the formulation comprises pH regulating agent.

In some embodiments of the invention, the formulation comprises pH regulating agent in an amount of 2.7 to 5.7% by weight of said formulation.

In some embodiments of the invention, the pH regulating agent comprises buffer.

As can be seen in table 1 and 3A-3F, sodium carbonate is used as a buffering agent. Usable buffering agents include carbonate, including monocarbonate, bicarbonate and sesquicarbonate, glycerinate, phosphate, glycerophosphate, acetate, glyconate or citrate of an alkali metal, ammonium, tris buffer, amino acids and mixtures thereof. Encapsulated buffer such as Effersoda may also be used.

In some embodiments, the formulation comprises buffering agent in an amount of from 2.7 to 5.7% by weight of the formulation.

The buffering agent may be added to the formulation together with the water-soluble fast disintegrating tablet ingredients.

When buffering agent is added to the fast disintegrating tablet as part of the water-soluble fast disintegrating tablet ingredients, a pH-profile according to embodiments of the present invention can be obtained.

Buffering agent in the tablet may be used to obtain the desired pH-values in the saliva of a tablet user.

In some embodiments, the buffering agent comprises sodium carbonate and sodium bicarbonate, e.g. in a weight-ratio between 5:1 and 2.5:1, preferably in a weight-ratio between 4.1:1 and 3.5:1.

A high suitable buffering agent according to advantageous embodiments of the present invention is the sodium carbonate-sodium bicarbonate buffer system.

As can be seen in table 1, silicon dioxide is used as a glidant. Other glidants usable for the formulation may also be used within the scope of the invention.

As can be seen in table 1 and 3A-3F, magnesium stearate is used as a lubricant. Other lubricants usable for the formulation may also be used within the scope of the invention.

As can be seen in table 3A-3F, ready to use systems may be used. Typically, such ready-to-use systems may e.g. replace filler, disintegrant, glidant or similar with a single powder mix. Suitable ready-to-use systems for the purpose, but not limited to, include Pearlitol Flash (Roquette), Pharmaburst 500 (SPI Pharma), Ludiflash (BASF), ProSolv (JRS Pharma), ProSolv EasyTab (JRS Pharma), F-Melt (Fuji Chemical), SmartEx50 or SmartEx100 (Shin Etsu/Harke Pharma).

In order to obtain a tablet being designed for disintegrating within a period of 60 second upon oral administration, a range of parameters can be adjusted.

First, by varying the composition, the disintegration time can be altered. Using ingredients with a high water-solubility may facilitate a lowered disintegration time.

Particularly, including a disintegrant may significantly influence the disintegration time, subject to the total composition. Also, by varying the amount and type of the disintegrant, the disintegration time may be further adjusted. For example, if a tablet having a lower disintegration time is desired, the percentage content of disintegrant may be increased and/or the type of disintegrant may be at least partly exchanged for a more effective disintegrant.

Also, decreasing the particle size of the disintegrant tends to lower the disintegration time, likely due to an increased surface area to volume ratio.

Furthermore, the compression force used in compressed tablets correlate significantly with the obtained hardness, such that a high compression force typically increases the hardness of the obtained tablet. By adjusting the hardness of a tablet, the disintegration time may also be influenced, such that a lowered hardness typically gives a shorter disintegration time. Here it has been observed for a number of compositions that by applying the correct compression force a disintegration time below 60 second upon oral administration can be achieved, whereas a too high compression force may result in a longer disintegration time above 60 seconds. In this regard it is noted that the threshold compression force may vary significantly, depending on other parameters, such as overall composition, content and type of disintegrant, etc. When, for example, a certain setup results in a too slow disintegration, a further way of adjusting may be to replace a regular disintegrant with a superdisintegrant, i.e. which facilitates disintegration in a more efficient way.

Increasing the water-solubility may also be facilitated by exchanging ingredients with low water-solubility with ingredients having higher water-solubility. For example, using sugar alcohols as fillers may be very advantageous insofar that the sugar alcohols have a higher water solubility than alternative fillers.

Moreover, using sugar alcohols with a lower compactability leads to lower disintegration time. Too low compactability may compromise the mechanical strength of the tablet and lead to undesirably high friability and risk of cracks etc.

Further examples of parameters that may be adjusted in order to obtain a tablet being designed for disintegrating within a period of 60 second upon oral administration include size and shape of the tablet. The larger the tablet, the longer the disintegration time and thus release time of the nicotine and pH regulating agent.

For example, increasing the flatness (e.g. quantified by a diameter to height ratio) for a disc-shaped tablet typically increases disintegration time by increasing the surface-to-volume. As long as the tablet has a satisfactory mechanical strength, flatness may be increased.

Also, modifying the cross-sectional profile from a convex type tablet to a concave shaped tablet lowers the disintegration time. It is noted that this may to some degree lower the mechanical strength of the tablet, however, as long as it is satisfactory, pursuing the concave cross-section may help to increase disintegration and thus lower the disintegration time.

Also, when using binders, e.g. to obtain a higher cohesiveness and mechanical strength of the tablet, the amount of such binders may be decreased as much as possible to obtain a higher disintegration rate and thus a shorter disintegration time.

Furthermore, by adding a salivation agent to the tablet, an increased amount of saliva in the vicinity of the tablet may be facilitated, which again supports the dissolving and disintegration of the tablet to reduce the disintegration time.

Further, the type and amount of lubricant, if any, may be adjusted to optimize disintegration time. For example, using Sodium stearyl fumarate (SSF) typically leads to a lower disintegration time compared to when using magnesium stearate MgSt.

Thus, a wide range of parameters may be adjusted when designing a tablet designed for disintegrating within a period of 60 second upon oral administration.

Typically, the formulation comprises of ingredients selected from the group consisting of bulk sweeteners, fillers, ready to use systems, flavors, dry-binders, disintegrant, hereunder superdisintegrants, tabletting aids, anticaking agents, emulsifiers, antioxidants, enhancers, absorption enhancers, buffering agents, high intensity sweeteners, colors, glidants, lubricants, or any combination thereof. Absorption enhancers may include e.g. pH regulating agents, such as buffering agents, and mucoadhesive.

In an embodiment of the invention, the tablet core is provided with an outer coating.

In an embodiment of the invention, said outer coating is selected from the group consisting of hard coating, soft coating and edible film-coating or any combination thereof.

According to an embodiment of the invention, at least a part of the nicotine is adhered to dry-binder particles.

According to an embodiment of the invention, an amount of dry-binder is used to adhere nicotine to bulk sweetener.

According to an embodiment of the invention, said fast disintegrating tablet comprises one or more encapsulation delivery systems.

Example 3

In Vivo pH

The fast disintegrating tablets are designed to have an in vivo pH higher than the resting saliva pH in the mouth. Thus, pH is measured in vivo, as follows:

At least 6 individuals chewed on a gum base free of buffer for 1 minute, after which the initial pH in a sample from the saliva from each of the individuals is measured with a suitable pH-electrode system, e.g. a stainless-steel electrode PHW77-SS. Only individuals having, after chewing on a gum base free of buffer for one minute, an initial pH in the saliva inside the range from 6.7 and 7.3 are selected. These individuals thereby qualify as average individuals.

One tablet is administered sublingually to at least six individuals. Hereafter, the saliva pH from each of the six individuals is measured at specified time intervals. Thus, each pH-value is the arithmetic mean of six measurements performed on saliva-samples from six individuals.

The sample volume of the individual saliva-samples may vary because the volume of saliva obtained may be different from each individual. This difference in sample volume does not affect the pH-measurements significantly. Also, it has been established by appropriate tests that a variation in time between collections of samples does not significantly alter the result. This means that the measured pH-value after three minutes is not significantly affected by whether another saliva-sample is taken from the six individuals e.g. after two minutes or not. Furthermore, it has been established by appropriate tests that the time from taking a sample to the time of measuring is not critical to the measured value. However, in the present measurements, the pH-values were measured in the samples within at most 15 minutes of sample collection.

The results are shown in table 3G.

TABLE 3G

In vivo pH. Nicorette Microtab (2 mg), Nicotinell Mint Lozenge (2 mg), and Nicotinell Mint Chewing gum (2 mg) were commercially available products.

| | pH | | | |
|---|---|---|---|---|
| | 10 sec | 20 sec | 90 sec | DT (sec) |
| FDT (12) (1 mg) | 9.3 | 9.1 | 8.4 | 20 |
| FDT (14) (1 mg) | 7.4 | 7.2 | 7.6 | 210 |
| FDT (13) (1 mg) | 5.3 | 5.8 | 6.5 | 15 |
| Nicorette Microtab (2 mg) | 6.7 | 6.8 | 6.8 | >600 |
| Nicotinell Mint Lozenge (2 mg) | 6.9 | 7.1 | 7.2 | >600 |
| Nicotinell Mint Chewing gum (2 mg) | 7.2 | 7.4 | 7.6 | NA |

As can be seen from table 3G, the pH exceeds 7.5 for FDT 12 and 13. For FDT 12, this even applies already at 10 and 20 seconds from contact with oral saliva. FDT(13), made without any buffer, did not give a pH above 7.5.

The needed raise in saliva pH is at least 0.5-1.0 pH units. A conventional nicotine mouth spray was chosen for comparison as well as Nicorette Microtab, Nicotinell Mint Lozenge, and Nicotinell Mint chewing gum. The conventional nicotine mouth spray reveals also fast craving relief. The conventional nicotine mouth spray raises the pH in saliva up to a maximum of 8.5 according to internal measurements. None of Nicorette Microtab and Nicotinell Mint Lozenge resulted in pH above 7.2. Nicotinell Mint chewing gum did not result in pH above 7.6.

The sample volume of the individual saliva-samples may vary because the volume of saliva obtained may be different from each individual. This difference in sample volume does not affect the pH-measurements significantly.

It should be noted that the in vivo pH would be different from an in vitro pH due to the fact that acidic sodium bicarbonate is normally continuously produced in saliva, hence neutralizing the alkaline contribution from buffer. Thus, the pH obtained in vivo will be lower than in vitro measured by e.g. dissolving the tablet in a beaker.

Example 4

Disintegration of Nicotine Tablets

The in vitro disintegration of the fast disintegrating tablets of example 1 and 2 was carried out in accordance to European Pharmacopeia 9.0, section 2.9.1, Disintegration of tablets and capsules. As described in the examples each batch has been manufactured in various tablet sub lots where the compression force has been varied and therefore the output parameters like hardness and friability will also vary. These output parameters do also have an impact on in vitro disintegration. The results for example 1 are outlined in table 4. A minimum and a maximum value for measured disintegration are given and this is more or less a function of the hardness.

TABLE 4

In vitro disintegration, hardness, friability. Time is given in seconds.

| | Mean in vitro disintegration (sec) | | Mean hardness (N) | | Mean friability (%) | |
|---|---|---|---|---|---|---|
| | Min (sec) | Max (sec) | Min (N) | Max (N) | Min (%) | Max (%) |
| FDT(a) | 21 | 24 | 14 | 63 | 0.0 | 0.3 |
| FDT(b) | 23 | 98 | 12 | 50 | 0.0 | 0.6 |
| FDT(c) | 29 | 177 | 14 | 55 | 0.0 | 0.5 |
| FDT(d) | 15 | 177 | 19 | 62 | 0.0 | 0.0 |

TABLE 4-continued

In vitro disintegration, hardness, friability.
Time is given in seconds.

|  | Mean in vitro disintegration (sec) | | Mean hardness (N) | | Mean friability (%) | |
| --- | --- | --- | --- | --- | --- | --- |
|  | Min (sec) | Max (sec) | Min (N) | Max (N) | Min (%) | Max (%) |
| FDT(e) | 13 | 175 | 15 | 45 | 0.0 | 0.2 |
| FDT(f) | 11 | 259 | 14 | 43 | 0.0 | 0.2 |

The above table should be interpreted as illustrated in the following example. When looking at e.g. FDT(a), the minimum mean disintegration time of 21 seconds correspond to a tablet pressed just hard enough to obtain a cohesive tablet having a minimum mean hardness of 14 N and a friability of 0.3%. Similarly, the maximum mean disintegration time of 24 seconds correspond to another tablet pressed harder to have a maximum mean hardness of 63 N. In this way, the tablet having a mean friability of 0.0% of FDT(a) corresponds to the tablet having a mean hardness of 63 N. In other words, in table 4 FDT(a) refers to two different tablets pressed at two different pressures, the linking being indicated above. I.e. each line corresponds to two different tablets, one for Min values of disintegration time and hardness and the Max value for friability, and another for Max values of disintegration time and hardness and the Min value for friability.

The results for example 2 are outlined in table 5.

TABLE 5

In vitro disintegration, hardness, friability.
Time is given in seconds.

|  | Mean in vitro disintegration (sec) | | Mean hardness (N) | | Mean friability (%) | |
| --- | --- | --- | --- | --- | --- | --- |
|  | Min (sec) | Max (sec) | Min (N) | Max (N) | Min (%) | Max (%) |
| FDT(g) | 120 | 210 | 17 | 22 | N/A | 0.5 |
| FDT(h) | 40 | 80 | 16 | 24 | 0.5 | 0.8 |
| FDT(i) | 10 | 46 | 17 | 22 | 0.3 | 0.3 |
| FDT(j) | 42 | 150 | 17 | 22 | 0.7 | 1.0 |
| FDT(k) | 45 | 201 | 17 | 22 | 0.6 | 0.9 |

The above table should be interpreted as illustrated in the example below table 4.

It is seen that the in vitro disintegrating may vary a lot between the disclosed fast disintegrating tablets. Hereby a disintegration profile as desired may be used together with a high in vivo pH (as described in example 3), whereby the nicotine may be more efficiently used. Most preferable an in vitro disintegrating profile below 60 seconds is desired since it would ensure a high concentration of nicotine combined with relatively high in vivo pH.

The in vitro disintegration is a fast method to determine the time and mechanism for tablet performance. More preferable or in combination the in vivo disintegration is measured. The in vivo disintegration time is a value for the actual disintegration of the sublingual tablet under the tongue. Table 6 and 7 highlights the results for in vivo disintegration.

TABLE 6

In vivo disintegration. Time is given in seconds.

|  | Mean in vivo disintegration (sec) | |
| --- | --- | --- |
|  | Min (sec) | Max (sec) |
| FDT(a) | 34 | 52 |
| FDT(b) | 18 | 27 |
| FDT(c) | 37 | N/A |
| FDT(d) | 42 | N/A |
| FDT(e) | 46 | N/A |

TABLE 7

In vivo disintegration. Time is given in seconds.

|  | Mean in vivo disintegration (sec) | |
| --- | --- | --- |
|  | Min (sec) | Max (sec) |
| FDT(g) | 19 | 40 |
| FDT(h) | 13 | 48 |
| FDT(i) | 32 | 80 |
| FDT(j) | N/A | 56 |
| FDT(k) | N/A | 81 |

The above tables 6-7 should be interpreted as illustrated in the example below table 4.

As recognized for the in vitro disintegration results above the speed of in vivo disintegrating may be varied between the disclosed batches. The disintegration time should be complete within 60 seconds from the onset of disintegration or preferable faster.

Since dissolution of nicotine bitartrate is a relatively fast process, the time used to release the content of nicotine can be taken as the disintegration time of the matrix (here the tablet).

Example 5

Nicotine Release and Absorption

Measurements of nicotine concentration is performed as follows:

One dose of the tablets of example 1 and 2 is administered sublingually to at least six individuals. At specified time intervals, the saliva is collected. The experiment is repeated. Thus, each nicotine concentration value is the arithmetic mean of 12 measurements, i.e. performed on saliva-samples from six individuals times 2. The nicotine concentration of saliva is analyzed on HPLC after extraction into relevant buffer.

Results are shown in tables 8A-8C.

TABLE 8A

Amount of nicotine in saliva.

|  | Measuring time from initial contact with oral saliva [seconds] | | |
| --- | --- | --- | --- |
|  | 10 | 20 | 90 |
|  | Concentration of nicotine [mg/mL] | | |
| 2 mg Nicotinell Mint Lozenge | 0.06 | 0.05 | 0.10 |
| 1 mg FDT (12) | 0.52 | 0.59 | 0.52 |
| 1 mg FDT (13) | 0.74 | 0.66 | 0.66 |
| 1 mg FDT (14) | 0.36 | 0.39 | 0.33 |

TABLE 8A-continued

Amount of nicotine in saliva.

| | Measuring time from initial contact with oral saliva [seconds] | | |
|---|---|---|---|
| | 10 | 20 | 90 |
| | Concentration of nicotine [mg/mL] | | |
| Nicorette Microtab 2 mg | 0.03 | 0.05 | 0.13 |
| Nicotinell Mint Chewing gum (2 mg) | 0.02 | 0.04 | 0.18 |

N/A = Not applicable (not assessed)

TABLE 8B

Amount of nicotine in residue.

| | Measuring time from initial contact with oral saliva [seconds] | | |
|---|---|---|---|
| | 10 | 20 | 90 |
| | Concentration of nicotine [mg/mL] | | |
| 2 mg Nicotinell Mint Lozenge | 1.90 | 1.91 | 1.85 |
| 1 mg FDT (12) | No residue | No residue | No residue |
| 1 mg FDT (13) | No residue | No residue | No residue |
| 1 mg FDT (14) | N/A | N/A | No residue |
| Nicorette Microtab 2 mg | 1.90 | 1.87 | 1.77 |
| Nicotinell Mint Chewing gum (2 mg) | 1.98 | 1.96 | 1.72 |

N/A = Not applicable (not assessed)

TABLE 8C

Absorption of nicotine.

| | Measuring time from initial contact with oral saliva [seconds] | | |
|---|---|---|---|
| | 10 | 20 | 90 |
| | Absorption of nicotine [% by weight] | | |
| 2 mg Nicotinell Mint Lozenge | 2 | 2 | 3 |
| 1 mg FDT (12) | 48 | 41 | 48 |
| 1 mg FDT (13) | 26 | 34 | 35 |
| 1 mg FDT (14) | N/A | N/A | 67 |
| Nicorette Microtab 2 mg | 4 | 4 | 5 |
| Nicotinell Mint Chewing gum (2 mg) | 0 | 0 | 5 |

N/A = Not applicable (not assessed)

As can be seen from table 8A-8C, formulations of the invention provided very high absorption, above 40% or even above 50%. Also, since FDT 1 and 2 are comparable, only that FDT 2 does not contain buffer, the effect of inclusion of the buffer may be observed. It is noted that FDT1 has a final absorption being significantly higher than FDT2, illustrating how inclusion of buffer increases the absorption of nicotine. Also, It is observed that the absorption of nicotine is more or less constant at times 10 seconds, 20 seconds, and 90 seconds, illustrating how the disintegration time (about seconds for FDT 1) is the limiting factor, and that the time for release of nicotine after disintegration as well as the time for absorption of nicotine is negligible for the present compositions.

The tablets of the example 1 and 2 are highly suitable to obtain orally disintegrating nicotine tablets for nicotine craving relief comprising a pressed powder formulation, the tablet being designed to disintegrate within a period of less than 60 seconds upon oral administration, the powder formulation comprising an amount of nicotine and a pH regulating agent.

Example 6

Evaluation of Fast Disintegrating Tablets—Burning

In general experiments have disclosed that nicotine fast disintegrating tablets according to the invention result in high absorption efficiency of nicotine into the blood stream for a fast disintegrating tablet user. With such fast integration, high pH-value combined with high nicotine concentration, only a minor part of the nicotine is swallowed by the user instead of entering the blood system, thereby resulting in fast craving relief.

When pH in the mouth is high, the nicotine is used in a very efficient way. However, too high pH in the saliva of the fast disintegrating tablet users may not be desirable, since the highly alkaline pH-value results in problems with irritation and burning of the sublingual tissue.

Consequently, the fast disintegrating tablets of the invention are indeed suitable in that they provide an efficient utilization of nicotine and at the same time are pleasant to the user, i.e. with clearly diminished unwanted side effects, hereunder particularly so called nicotine burning in the throat.

Evaluation of burning sensation is performed as described in the following.

Nicotine burning was evaluated by a test panel of 7 trained assessors. After calibration by means of chewing two standard nicotine containing chewing gum with "known" burning intensity, each assessor evaluates the burning sensation in the throat on a scale from 1 to 15, where 15 is the most intense burning. Each assessor evaluates all samples twice. The evaluations are noted for the time periods indicated. Average values are calculated.

TABLE 9

Sensory evaluation of throat burning.

| | Time [seconds] | | |
|---|---|---|---|
| | 145 | 295 | 505 |
| | Burning score (1-15) | | |
| FDT (12) | 3.5 | 1.8 | 0.8 |
| FDT (14) | 6.6 | 4.5 | 2.7 |
| Nicotinell Mint Chewing gum (2 mg) | 4.6 | 4.6 | 3.4 |
| Nicotinell Mint Lozenge (2 mg) | 4.8 | 4.9 | 4.2 |
| Nicorette Microtab (2 mg) | 6.4 | 5.9 | 5.5 |

Example 7—Alleviation of Nicotine Craving

Nicotine craving alleviation was tested using a panel of three users evaluating all samples twice. Each user noted the time from oral administration until craving relief, i.e. feeling the effect of nicotine reaching the head. The average times for FDT (12) and FDT (14) and three commercially available products are indicated in table 10.

TABLE 10

Time before alleviation.

| Time before alleviation | FDT (12) | FDT (14) | Nicotinell Mint Chewing gum (2 mg) | Nicotinell Mint Lozenge (2 mg) | Nicorette Microtab (2 mg) |
|---|---|---|---|---|---|
| Average | 240 | 300 | 560 | 480 | 400 |

As can be seen from table 10, significantly faster alleviation was obtained compared to the commercially available products.

The invention claimed is:

1. An orally disintegrating nicotine tablet for nicotine craving relief comprising a pressed powder formulation, wherein the tablet disintegrates within a period of less than 210 seconds upon oral administration, wherein the pressed powder formulation comprises an amount of nicotine, a pH regulating agent, at least one polyol, and a disintegrant wherein the tablet comprises the polyol in an amount of more than 40% by weight of the tablet, wherein the tablet comprises the disintegrant in an amount of 1-10% by weight of the tablet, wherein the formulation provides a peak saliva pH of more than 7.6 during the first 120 seconds upon oral administration, wherein at least 40% by weight of the nicotine is absorbed through the oral mucosa, and wherein the tablet substantially reduces the side effect of burning.

2. The tablet according to claim 1, wherein the tablet is designed to disintegrate within a period of less than 60 seconds upon oral administration.

3. The tablet according to claim 1, wherein the tablet comprises nicotine in an amount of at least 0.5 mg.

4. The tablet according to claim 1, wherein said nicotine is provided as a nicotine salt.

5. The tablet according to claim 4, wherein the nicotine salt is selected from nicotine ascorbate, nicotine aspartate, nicotine benzoate, nicotine monotartrate, nicotine bitartrate, nicotine chloride, nicotine citrate, nicotine fumarate, nicotine gensitate, nicotine lactate, nicotine mucate, nicotine laurate, nicotine levulinate, nicotine malate nicotine perchlorate, nicotine pyruvate, nicotine salicylate, nicotine sorbate, nicotine succinate, nicotine zinc chloride, nicotine sulfate, nicotine tosylate, nicotine salt hydrates, and any combination thereof.

6. The tablet according to claim 1, wherein said nicotine is provided as a complex between nicotine and an ion exchange resin.

7. The tablet according to claim 1, wherein said nicotine is provided in ionic complex with at least one mucoadhesive water-soluble anionic polymer.

8. The tablet according to claim 1, wherein the tablet is a sublingual tablet.

9. The tablet according to claim 1, wherein the pressed powder comprises at least one polyol and wherein the polyol comprises more than 59% by weight of the tablet.

10. The tablet according to claim 1, wherein the tablet is pressed at a pressure of 2-20 kN.

11. The tablet according to claim 1, wherein the formulation provides a peak saliva concentration of nicotine of more than 0.3 mg/mL and a peak saliva pH of more than 8 during the first 120 seconds upon oral administration.

12. The tablet according to claim 1, wherein the tablet comprises sodium stearyl fumarate (SSF) as a lubricant.

13. The tablet according to claim 1, wherein the tablet comprises pH regulating agent in an amount of at least 2.7 percent by weight of said tablet.

14. The tablet according to claim 1, wherein the tablet has a weight of 25 to 200 mg.

15. The tablet according to claim 1, wherein the at least one polyol is selected from the group consisting of sorbitol, erythritol, xylitol, maltitol, mannitol, lactitol, isomalt, and any combination thereof.

16. The tablet according to claim 1, wherein the at least one polyol is mannitol.

17. The tablet according to claim 1, wherein the disintegrant is selected from the group consisting of starch, pregelatinated starch, modified starch, cellulose, microcrystalline cellulose, alginates, ion-exchange resin, superdisintegrants, and combinations thereof.

18. The tablet according to claim 1, wherein the disintegrant is selected from the group consisting of crosslinked cellulose, crosslinked polyvinyl pyrrolidone (PVP), crosslinked starch, crosslinked alginic acid, natural superdisintegrants, calcium silicate, and combinations thereof.

19. The tablet according to claim 1, wherein the disintegrant comprises at least one of crospovidone, sodium starch glycolate, and croscarmellose.

20. An orally disintegrating nicotine tablet for nicotine craving relief comprising a pressed powder formulation, wherein the tablet disintegrates within a period of less than 210 seconds upon oral administration, wherein the pressed powder formulation comprises an amount of nicotine, a pH regulating agent, at least one polyol, and a disintegrant wherein the tablet comprises the polyol in an amount of more than 40% by weight of the tablet, wherein the tablet comprises the disintegrant in an amount of 1-10% by weight of the tablet, wherein the formulation provides a peak saliva pH of more than 7.6 during the first 120 seconds upon oral administration, wherein at least 40% by weight of the nicotine is absorbed through the oral mucosa, and wherein the tablet provides alleviation of nicotine craving within a period of no more than 300 seconds upon oral administration.

21. An orally disintegrating nicotine tablet for nicotine craving relief comprising a pressed powder formulation, wherein the tablet disintegrates within a period of less than 210 seconds upon oral administration, wherein the pressed powder formulation comprises an amount of nicotine, a pH regulating agent, at least one polyol, and a disintegrant wherein the tablet comprises the polyol in an amount of more than 40% by weight of the tablet, wherein the tablet comprises the disintegrant in an amount of 1-10% by weight of the tablet, wherein the formulation provides a peak saliva pH of more than 7.6, wherein at least 40% by weight of the nicotine is absorbed through the oral mucosa, and wherein the tablet reduces the side effect of burning.

22. A method of alleviation of nicotine craving by administering said orally disintegrating nicotine tablet according to claim 1.

* * * * *